United States Patent
Fu et al.

(10) Patent No.: US 11,447,458 B2
(45) Date of Patent: Sep. 20, 2022

(54) TANNIC ACID CURING AGENT AND PREPARATION METHOD AND APPLICATION THEREOF

(71) Applicant: Jiangxi Science and Technology Normal University, Nanchang (CN)

(72) Inventors: Changqing Fu, Nanchang (CN); Liang Shen, Nanchang (CN); Yaqi Hu, Nanchang (CN)

(73) Assignee: Jiangxi Science and Technology Normal University, Nanchang (CN)

( * ) Notice: Subject to any disclaimer, the term of this patent is extended or adjusted under 35 U.S.C. 154(b) by 114 days.

(21) Appl. No.: 17/161,706

(22) Filed: Jan. 29, 2021

(65) Prior Publication Data
US 2022/0242842 A1 Aug. 4, 2022

(51) Int. Cl.
*C07D 309/10* (2006.01)
*C08G 59/62* (2006.01)

(52) U.S. Cl.
CPC ......... *C07D 309/10* (2013.01); *C08G 59/621* (2013.01)

(58) Field of Classification Search
CPC .............................. C08G 59/621; C07D 309/10
USPC ........................................................ 528/98
See application file for complete search history.

(56) References Cited

FOREIGN PATENT DOCUMENTS

CN         110790902 A  *  2/2020  ............... C07H 1/00

OTHER PUBLICATIONS

Fu et al., CN 110790902 A machine translation in English, Feb. 14, 2020 (Year: 2020).*

* cited by examiner

*Primary Examiner* — David T Karst
(74) *Attorney, Agent, or Firm* — Bayramoglu Law Offices LLC (57) ABSTRACT

A tannic acid curing agent and a preparation method thereof are provided. The present invention uses tannic acid as a raw material and the long fatty chain of 10-undecenoyl chloride is introduced into the tannic acid structure to obtain the tannic acid curing agent. The preparation method includes the following steps: mixing tannic acid, 10-undecenoyl chloride, a catalyst and a solvent for a substitution reaction to obtain undecylenyl tannic acid, in which the catalyst includes an acid binding agent and 4-diaminopyridine, and the solvent includes ethyl acetate and N,N-dimethylformamide; mixing the undecylenyl tannic acid, a mercapto compound, a solvent and a photoinitiator for an addition reaction under an ultraviolet irradiation to obtain the tannic acid curing agent, in which the mercapto compound is a mercapto carboxylic acid compound or a mercapto alcohol compound.

12 Claims, 4 Drawing Sheets

TANNIC ACID CURING AGENT AND PREPARATION METHOD AND APPLICATION THEREOF

TECHNICAL FIELD

The present invention belongs to the technical field of curing agents for epoxy resin, and in particular to a tannic acid curing agent and a preparation method and an application thereof.

BACKGROUND

As one of the three thermosetting resins, epoxy resin has many excellent properties, such as excellent adhesion to many substrates, high strength, low shrinkage, excellent chemical resistance, corrosion resistance, good processability and low cost; so it is used in coatings, adhesives, composites, electronic materials and other fields. However, epoxy resin has a thermoplastic linear structure, which cannot be directly used to form a film. A curing agent must be added to the resin to form a film by chemical cross-linking. The common types of curing agents for epoxy resin on the market are polyamines, anhydrides, polyphenols, polymercaptans, etc., most of which are made from petroleum resources. However, with the increasing depletion of the petroleum resources, sustainability has become the theme of social development, and biomaterials have become one of the hot spots of new materials worldwide. Biological resources have the advantages of low cost, easy availability and are renewable. The application of bio-based raw materials instead of traditional petroleum raw materials in the epoxy field has become a major challenge in the development of new epoxy resins.

In addition, the brittleness of epoxy resin limits its application, so the toughening process of epoxy resin has become a key and difficult point in epoxy research. There are two common toughening methods for epoxy resin. The first method is to add toughening agents in an epoxy system, and the toughening agents include rubber, thermoplastic resin, liquid crystal polymer, hyperbranched polymer, etc. These toughening agents can exist in the cross-linking network in the form of particles or granules, and can also form an interpenetrating network with epoxy resin to toughen epoxy resin by reaching microphase separation. The key problem to be solved in the method of adding toughening agents is to address the compatibility of resin and toughening agent. If the compatibility of resin and toughening agent is poor, it is prone to demulsification, shrinkage cavity and other problems. The second method is to add reactive toughening agents into the epoxy system to introduce the flexible segments of the toughening agents into the curing network to increase the mobility of network segments. However, most of the reactive toughening agents on the market have the disadvantage of high viscosity. When mixing with the epoxy system, a large amount of solvent needs to be added or a high temperature is required for uniform mixing.

In conclusion, the raw materials used in the preparation of curing agents in the prior art are not biomaterials, and the obtained curing agents have single performance, which cannot toughen the epoxy resin.

SUMMARY

The objective of the present invention is to overcome the defects of the prior art and to provide a curing agent which is mainly composed of bio-based raw materials and can toughen an epoxy resin.

In order to achieve the above objective of the present invention, the present invention provides the following technical solution.

The present invention provides a preparation method of a tannic acid curing agent, including the following steps:

(1) mixing tannic acid, 10-undecenoyl chloride, a catalyst and a solvent for a substitution reaction to obtain undecylenyl tannic acid;

wherein the catalyst includes an acid binding agent and 4-diaminopyridine; and the solvent includes ethyl acetate and N,N-dimethylformamide;

(2) mixing the undecylenyl tannic acid, a mercapto compound, the solvent and a photoinitiator for an addition reaction under an ultraviolet irradiation to obtain the tannic acid curing agent;

wherein the mercapto compound is a mercapto carboxylic acid compound or a mercapto alcohol compound.

Preferably, a molar ratio of the tannic acid and the 10-undecenoyl chloride in step (1) is 1:30-50, and a mass ratio of the tannic acid and the N,N-dimethylformamide is 1:7-10.

Preferably, a mass ratio of the N,N-dimethylformamide and the ethyl acetate in step (1) is 1:1.5-2.5; a mass ratio of the acid binding agent and the ethyl acetate is 1:6-8; and a mass ratio of the 4-diaminopyridine and the acid binding agent is 1:19-22.

Preferably, a reaction temperature of the substitution reaction in step (1) is 30-40° C., a reaction time is 20-30 h, and the substitution reaction is carried out in a protective atmosphere.

Preferably, the mercapto carboxylic acid compound is at least one selected from the group consisting of mercaptoacetic acid, 3-mercaptopropionic acid, thiolactic acid, (2S)-2-thio, 2-mercapto-2-methylpropionic acid, 4-mercaptobutyric acid, 3-mercaptoisobutyric acid, cysteine, DL-cysteine, D-cysteine, 4-thiovaleric acid, 3-amino-2-thiopropionic acid, 6-mercaptoacetic acid and 4-mercapto-4-methylvaleric acid.

Preferably, the mercapto alcohol compound is at least one selected from the group consisting of 2-mercaptoethanol, 3-mercapto-1-propanol, 1-mercapto-2-propanol, 2-mercapto-1-propanol, 2-mercapto-3-butanol, 4-mercapto-1-butanol, 3-mercapto-2-butanol, 1-thioglycerol, (S)-1-thioglycerol and 3-mercapto-3-methyl-1-butanol.

Preferably, a molar ratio of the undecylenyl tannic acid and the mercapto compound in step (2) is 1:12-21, the photoinitiator is a UV series initiator, an addition amount of the photoinitiator is 0.5-2 wt % of a total mass of the mercapto compound and the undecylenyl tannic acid, the solvent includes methylene chloride, the ethyl acetate and ethanol, and a mass ratio of the tannic acid and the solvent is 1:1-5.

Preferably, parameters of the ultraviolet irradiation are as follows: an irradiance is 5,000-7,000 µW/cm$^2$, a wavelength is 350-395 nm, an irradiation time is 10-14 h.

The present invention also provides a tannic acid curing agent obtained by the preparation method.

The present invention also provides an application of the tannic acid curing agent in toughening an epoxy resin, in which the epoxy resin is glycidyl ether epoxy resin, glycidyl ester epoxy resin or heterocyclic epoxy resin.

The present invention provides the tannic acid curing agent. Raw materials used for common curing agents are petroleum resources, which are not sustainable. The curing agent of the present invention uses tannic acid as a raw material, the long fatty chain of 10-undecenoyl chloride is introduced into the tannic acid structure, and the content of renewable carbon contained in the tannic acid and undecenyl group of the curing agent product reaches 85-93%.

The present invention also provides the preparation method of the tannic acid curing agent. The preparation method provided by the present invention has extremely simple operation, universality and is suitable for mass production.

The present invention also provides the application of the tannic acid curing agent in toughening an epoxy resin, which can greatly improve the toughness of glycidyl ether epoxy resin, glycidyl ester epoxy resin and heterocyclic epoxy resin. The benzene ring structure contained in the curing agent can increase the rigidity of the epoxy film. The long fatty chain of undecenyl group takes part in the curing reaction, which increases the mobility of the network segment and greatly improves the toughness of the epoxy resin. According to the experiment, the deformation of the obtained epoxy resin can reach 60% under the stress of 5.5 Mpa.

DETAILED DESCRIPTION OF THE EMBODIMENTS

The present invention provides a preparation method of a tannic acid curing agent, which is implemented by the following steps.

(1) Tannic acid, 10-undecenoyl chloride, a catalyst and a solvent are mixed for a substitution reaction to obtain undecylenyl tannic acid;

the catalyst includes an acid binding agent and 4-diaminopyridine; and the solvent includes ethyl acetate and N,N-dimethylformamide.

(2) The undecylenyl tannic acid, a mercapto compound, the solvent and a photoinitiator are mixed for an addition reaction under an ultraviolet irradiation to obtain the tannic acid curing agent;

the mercapto compound is a mercapto carboxylic acid compound or a mercapto alcohol compound.

In the present invention, the tannic acid, the 10-undecenoyl chloride, the catalyst and the solvent are mixed for the substitution reaction to obtain the undecylenyl tannic acid.

In the present invention, the catalyst includes the acid binding agent and the 4-diaminopyridine, the acid binding agent is triethylamine or tetrabutylammonium bromide. The inorganic acid binding agent in the system will combine with tannic acid to form agglomerates and ultimately malfunction. The acid binding agent combines with hydrogen chloride produced by the reaction to promote the reaction to proceed in the forward direction. The 4-diaminopyridine is a catalyst commonly used in acylation reaction. The solvent includes ethyl acetate and N,N-dimethylformamide, and the residual tannic acid is dissolved in the N,N-dimethylformamide, which can be removed by washing. The product obtained in the experiment is grafted with the undecenyl group, the polarity is reduced, and it is dissolved in ethyl acetate, which facilitates the extraction of the product. In the present invention, the substitution reaction is preferably carried out in a reactor, more preferably, tannic acid is first placed in the reactor, and then a mixed solvent consisting of ethyl acetate and N,N-dimethylformamide is added to dissolve the tannic acid, then the acid binding agent and 4-diaminopyridine are added in the reactor, and 10-undecenoyl chloride is put in a dropping funnel and dropwise added into the reactor for the substitution reaction. In the present invention, the 10-undecenoyl chloride is dropwise added at a rate of preferably 0.5-3 d/s, further preferably 1-2 d/s.

In the present invention, a molar ratio of the tannic acid and the 10-undecenoyl chloride in step (1) is 1:30-50, more preferably 1:35-48, and further preferably 1:40-45; a mass ratio of the tannic acid and the N,N-dimethylformamide is 1:7-10, and more preferably 1:8-9.

In the present invention, a mass ratio of the N,N-dimethylformamide and the ethyl acetate in step (1) is preferably 1:1.5-2.5, and further preferably 1:1.8-2.2; a mass ratio of the acid binding agent and the ethyl acetate is preferably 1:6-8, and further preferably 1:6.5-7.5; a mass ratio of the 4-diaminopyridine and the acid binding agent is 1:19-22, and further preferably 1:20-21.

In the present invention, a reaction temperature of the substitution reaction in step (1) is preferably 30-40° C., and further preferably 32-38° C.; a reaction time is preferably 20-30 h, and further preferably 25-30 h; the reaction time is counted after all the 10-undecenoyl chloride is added dropwise, and the protective atmosphere is preferably nitrogen or argon.

At the end of the substitution reaction, the product system is preferably suction filtered, washed, dried and rotary evaporated successively to obtain a pure and dry undecylenyl tannic acid. In the present invention, a detergent for washing is preferably saturated sodium bicarbonate, and a desiccant for drying is preferably anhydrous magnesium sulfate. The present invention has no special requirements for the implementation mode of the suction filtration and rotary evaporation, as long as the corresponding effects can be achieved. The pure and dry undecylenyl tannic acid obtained by the present invention is a yellow brown viscous liquid.

In the present invention, the substitution reaction in step (1) is specifically a substitution reaction between 10-undecenoyl chloride and a hydroxyl group in tannic acid. Chlorine of the 10-undecenoyl chloride combines with hydrogen of the hydroxyl group to generate hydrogen chloride, and the long chain of the 10-undecenoyl chloride is connected to oxygen atom of the hydroxyl group. The hydroxyl group of the tannic acid can react with at least one 10-undecenoyl chloride at random substitution positions.

As a specific reaction example of the present invention, the substitution reaction process is as follows:

(formula 1)

In formula 1, represents a branched chain group in the molecular structure of tannic acid.

After undecylenyl tannic acid is obtained, the undecylenyl tannic acid is mixed with the mercapto compound, the photoinitiator and the solvent to carry out the addition reaction under the ultraviolet irradiation.

In the present invention, the mercapto carboxylic acid compound is preferably at least one selected from the group consisting of mercaptoacetic acid, 3-mercaptopropionic acid, thiolactic acid, (2 S)-2-thio, 2-mercapto-2-methylpropionic acid, 4-mercaptobutyric acid, 3-mercaptoisobutyric acid, cysteine, DL-cysteine, D-cysteine, 4-thiovaleric acid, 3-amino-2-thiopropionic acid, 6-mercaptoacetic acid and 4-mercapto-4-methylvaleric acid.

In the present invention, the mercapto alcohol compound is preferably at least one selected from the group consisting of 2-mercaptoethanol, 3-mercapto-1-propanol, 1-mercapto-2-propanol, 2-mercapto-1-propanol, 2-mercapto-3-butanol, 4-mercapto-1-butanol, 3-mercapto-2-butanol, 1-thioglycerol, (S)-1-thioglycerol and 3-mercapto-3-methyl-1-butanol.

In the present invention, a molar ratio of the undecylenyl tannic acid and the mercapto compound is preferably 1:12-21, and further preferably 1:16-20. The photoinitiator is a UV series initiator, and further preferably UV1173. An addition amount of the photoinitiator is 0.5-2 wt % of a total mass of the mercapto compound and the undecylenyl tannic acid, and further preferably 1-1.5 wt %. The solvent in step (2) is preferably one selected from the group consisting of methylene chloride, the ethyl acetate and ethanol. A mass ratio of the tannic acid and the solvent in step (2) is preferably 1:1-5, and further preferably 1:2-4.

In the present invention, the ultraviolet irradiation is preferably provided by an ultraviolet lamp. An irradiance of the ultraviolet irradiation is preferably 5,000-7,000 µW/cm², and further preferably 5,500-6,500 µW/cm². A wavelength of the ultraviolet irradiation is preferably 350-395 nm, and further preferably 360-380 nm. An irradiation time of the ultraviolet irradiation is preferably 10-14 h, and further preferably 11-13 h.

In the present invention, the addition reaction in step (2) is specifically an addition reaction between undecylenyl tannic acid and the mercapto compound, which occurs at a carbon-carbon double bond of the undecylenyl tannic acid and a sulfhydryl group of the mercapto compound. At least one carbon-carbon double bond of the undecylenyl tannic acid can react with the mercapto compound at random addition positions.

As a specific reaction example of the present invention, the addition reaction process is as follows:

The present invention also provides the tannic acid curing agent obtained by the preparation method.

The present invention also provides an application of the tannic acid curing agent in toughening an epoxy resin.

The process of toughening the epoxy resin with the tannic acid curing agent of the present invention preferably includes the following steps:

the tannic acid curing agent, the epoxy resin and the catalyst are mixed and then subjected to stepwise heating and curing to obtain a toughened modified epoxy resin.

In the present invention, the epoxy resin preferably includes glycidyl ether epoxy resin, glycidyl ester epoxy resin or heterocyclic epoxy resin. A feeding ratio of the tannic acid curing agent and the epoxy resin is 1:0.5-2.5 according to a molar ratio of active hydrogen and epoxy equivalent, and further preferably 1:1-2.

In the present invention, the catalyst is preferably 2,4,6-tris(dimethylaminomethyl)phenol (DMP-30), N,N-diethylmethylamine, tetrabutylammonium bromide, triethylamine or tetramethylammonium fluoride. An addition amount of the catalyst is preferably 0.1-1 wt %, and further preferably 0.3-0.6 wt %, according to a percentage of a total mass of the tannic acid curing agent and the epoxy resin.

In the present invention, the stepwise heating and curing successively includes a first-stage curing, a second-stage curing and a third-stage curing. A temperature of the first-stage curing is preferably 40-60° C., and further preferably 45-55° C. A time of the first-stage curing is preferably 1-3 h, and further preferably 1.5-2.5 h. A temperature of the second-stage curing is preferably 70-90° C., and further preferably 75-85° C. A time of the second-stage curing is preferably 3-5 h, and further preferably 3.5-4.5 h. A temperature of the third-stage curing is 100-120° C., and further preferably 105-115° C. A time of the third-stage curing is 3-5 h, and further preferably 3.5-4.5 h.

The technical solutions provided by the present invention are described in detail in combination with the examples below, but they cannot be understood as limiting the protection scope of the present invention.

Example 1

Figure 1:
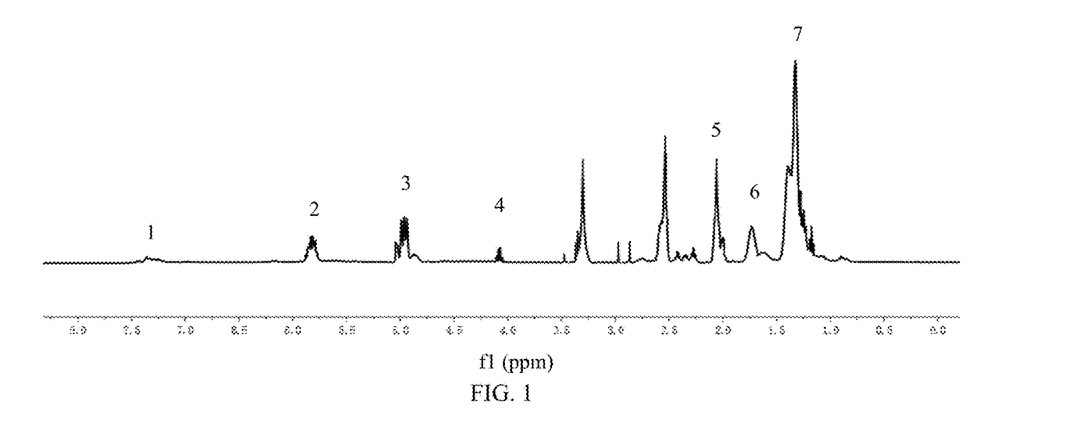
FIG. 1 is a hydrogen-1-nuclear magnetic resonance ($^1$H-NMR) spectrum of the undecylenyl tannic acid in example 1.
Figure 2:
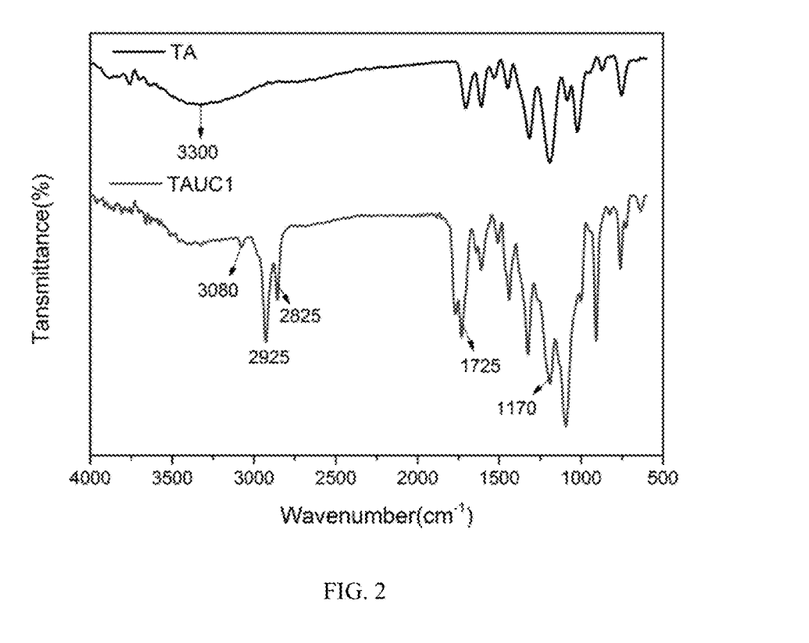
FIG. 2 is a diagram showing an infrared spectrum of the undecylenyl tannic acid and an infrared spectrum of the tannic acid in example 1.

3.4 g of tannic acid is put into a three-necked flask and dissolved with 30 g of N,N-dimethylformamide (DMF) and 50 g of ethyl acetate (EA). 7.581 g of triethylamine and 0.372 g of 4-diaminopyridine (DMAP) are added to the three-necked flask. The three-necked flask is placed in a 35° C. water bath for a magnetic stirring. 15.204 g of 10-undecenoyl chloride is diluted in a dropping funnel with another 5 g of the EA. The 10-undecenoyl chloride is dropwise added into the three-necked flask at a rate of 1 d/s. After ending the dropwise addition, the reaction is continued for 28 h. During the reaction, $N_2$ is introduced to prevent the tannic acid from being oxidized. At the end of the reaction, triethylamine hydrochloride is removed by a suction filtration, and the reaction product is washed with a saturated sodium bicarbonate aqueous solution for several times. The resulting organic phase is dried with anhydrous magnesium sulfate for 3 h, suction filtered, and rotary evaporated to obtain a yellow brown viscous oily liquid, namely undecylenyl tannic acid (TAUC 1). The $^1$H-NMR and Fourier Transform infrared (FT-IR) spectra of TAUC 1 are shown in FIG. 1 and FIG. 2 respectively, which can prove the structure of the undecylenyl tannic acid.

Figure 3:
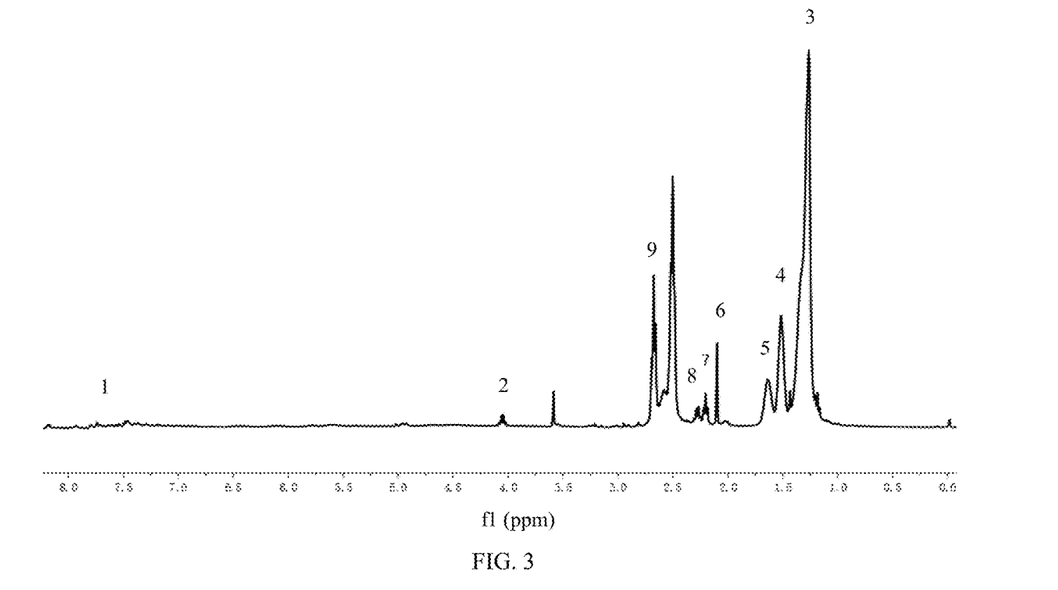
FIG. 3 is an $^1$H-NMR spectrum of the tannic acid curing agent in example 1.
Figure 4:
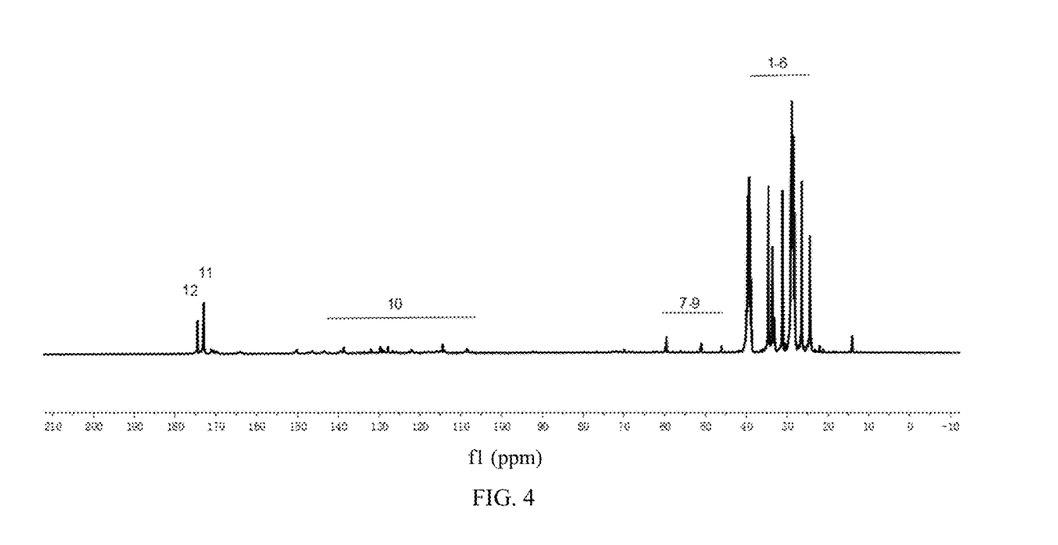
FIG. 4 is a carbon-13 ($^{13}$C)-NMR spectrum of the tannic acid curing agent in example 1.
Figure 5:
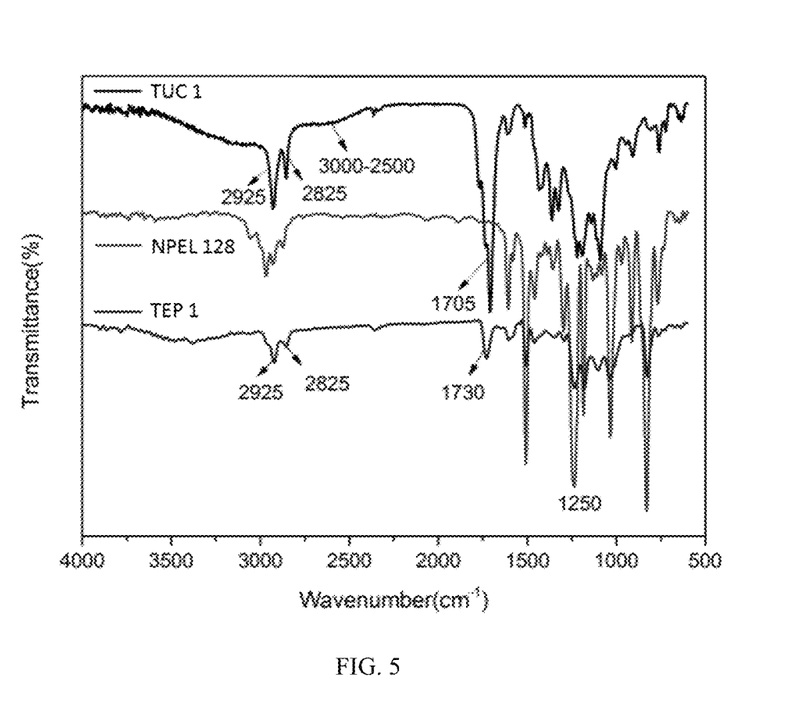
FIG. 5 is a diagram showing infrared spectra of the undecylenyl tannic acid, the tannic acid curing agent and the NPEL128 epoxy resin in example 1.

4 g of the TAUC 1 is put into a 50 ml single-necked flask and dissolved with 10 g of the EA, added with 1.583 g of 3-mercaptopropionic acid and 1 wt % of UV1173 and mixed evenly, and placed on a magnetic stirrer for a magnetic stirring. The reaction is carried out under a UV irradiation, and the reaction progress is monitored by infrared. When the double bond disappears, the reaction ends. The EA is removed by a rotary evaporator to obtain a light-yellow viscous liquid, namely a tannic acid curing agent (TUC 1). The $^1$H-NMR, $^{13}$C-NMR and FT-IR spectra of the TUC 1 are shown in FIG. 3, FIG. 4 and FIG. 5 respectively, which can prove the structure of the tannic acid curing agent.

3.70 g of epoxy resin NPEL 128 is mixed with 2.72 g of the TUC 1, and 1 wt % of tetrabutylammonium bromide is added as a catalyst, mixed evenly to prepare a tinplate coating plate with an actual film thickness of 120 μm to test the impact-resistance strength, bending, hardness and adhesion of the film. An epoxy film with a film thickness of 0.5 mm is prepared in the mould to test the stress-strain and modulus of the film. The tinplate and mould are cured in an oven at 60° C. for 3 h, then 80° C. for 4 h, and then 120° C. for 6 h to obtain an epoxy film, recorded as TEP 1.

Example 2

4.2 g of tannic acid is put into a three-necked flask and dissolved with 34 g of DMF and 50 g of EA. 9.088 g of tetrabutylammonium bromide and 0.432 g of DMAP are added to the three-necked flask. The three-necked flask is placed in a 35° C. water bath for a magnetic stirring. 18.244 g of 10-undecenoyl chloride is diluted in a dropping funnel with another 18 g of the EA. The 10-undecenoyl chloride is dropwise added into the three-necked flask at a rate of 1 d/s. After finishing the dropwise addition, the reaction is continued for 29 h. During the reaction, $N_2$ is introduced to prevent the tannic acid from being oxidized. At the end of the reaction, tetrabutylammonium bromide hydrochloride is removed by a suction filtration, the reaction product is washed with a saturated sodium bicarbonate aqueous solution for several times. Then the resulting organic phase is dried with anhydrous magnesium sulfate for 3 h, suction filtered, and rotary evaporated to obtain a yellow brown viscous oily liquid, namely undecylenyl tannic acid (TAUC 2).

4 g of the TAUC 2 is put into a 50 ml single-necked flask and dissolved with 10 g of ethanol, added with 1.662 g of mercaptoacetic acid and 1 wt % of UV1173 and mixed evenly, and placed on a magnetic stirrer for a magnetic stirring. The reaction is carried out under a UV irradiation, and the reaction progress is monitored by infrared. When the double bond disappears, the reaction ends. The ethanol is removed by a rotary evaporator to obtain a light-yellow viscous liquid, namely a tannic acid curing agent (TUC 2).

3.70 g of epoxy resin NPEL 128 is mixed with 2.61 g of the TUC 2, and 1 wt % of tetrabutylammonium bromide is added as a catalyst, mixed evenly to prepare a tinplate coating plate with an actual film thickness of 120 μm to test the impact-resistance strength, bending, hardness and adhesion of the film. An epoxy film with a film thickness of 0.5 mm is prepared in the mould to test the stress-strain and modulus of the film. The tinplate and mould are cured in an oven at 60° C. for 3 h, then 80° C. for curing for 3 h, and then 120° C. for 6 h to obtain an epoxy film, recorded as TEP 2.

Example 3

3.8 g of tannic acid is put into a three-necked flask and dissolved with 32.3 g of DMF and 50 g of EA. 8.613 g of tetrabutylammonium bromide and 0.453 g of DMAP are added to the three-necked flask. The three-necked flask is placed in a 35° C. water bath for a magnetic stirring. 12.163 g of 10-undecenoyl chloride is diluted in a dropping funnel with another 14.6 g of the EA. The 10-undecenoyl chloride is dropwise added into the three-necked flask at a rate of 1 d/s. After finishing the dropwise addition, the reaction is continued for 28 h. During the reaction, Ar is introduced to prevent the tannic acid from being oxidized. At the end of the reaction, tetrabutylammonium bromide hydrochloride is removed by a suction filtration, the reaction product is washed with a saturated sodium bicarbonate aqueous solution for several times. Then the resulting organic phase is dried with anhydrous magnesium sulfate for 3 h, suction filtered, and rotary evaporated to obtain a yellow brown viscous oily liquid, namely undecylenyl tannic acid (TAUC 3).

4 g of the TAUC 3 is put into a 50 ml single-necked flask and dissolved with 10 g of methylene chloride, added with 1.434 g of 3-mercaptopropionic acid and 1 wt % of UV1173 and mixed evenly, and placed on a magnetic stirrer for a magnetic stirring. The reaction is carried out under a UV irradiation, and the reaction progress is monitored by infrared. When the double bond disappears, the reaction ends. The methylene chloride is removed by a rotary evaporator to obtain a light-yellow viscous liquid, namely a tannic acid curing agent (TUC 3).

3.70 g of epoxy resin NPEL 128 is mixed with 4.03 g of the TUC 3, and 1 wt % of N,N-diethylmethylamine is added as a catalyst, mixed evenly to prepare a tinplate coating plate with an actual film thickness of 120 μm to test the impact-resistance strength, bending, hardness and adhesion of the film. An epoxy film with a film thickness of 0.5 mm is prepared in the mould to test the stress-strain and modulus of the film. The tinplate and mould are cured in an oven at 60° C. for 3 h, then 85° C. for 4.5 h, and then 115° C. for 5 h to obtain an epoxy film, recorded as TEP 3.

Example 4

3.6 g of tannic acid is put into a three-necked flask and dissolved with 27 g of DMF and 50 g of EA. 7.952 g of triethylamine and 0.378 g of DMAP are added to the three-necked flask. The three-necked flask is placed in a 40° C. water bath for a magnetic stirring. 17.231 g of 10-undecenoyl chloride is diluted in a dropping funnel with another 9.4 g of the EA. The 10-undecenoyl chloride is dropwise added into the three-necked flask at a rate of 1 d/s. After finishing the dropwise addition, the reaction is continued for 26 h. During the reaction, Ar is introduced to prevent the tannic acid from being oxidized. At the end of the reaction, triethylamine hydrochloride is removed by a suction filtration, the reaction product is washed with a saturated sodium bicarbonate aqueous solution for several times. Then the resulting organic phase is dried with anhydrous magnesium sulfate for 4 h, suction filtered, and rotary evaporated to obtain a yellow brown viscous oily liquid, namely undecylenyl tannic acid (TAUC 4).

4 g of the TAUC 4 is put into a 50 ml single-necked flask and dissolved with 9 g of methylene chloride, added with 1.434 g of 2-mercaptoethanol and 1 wt % of UV1173 and mixed evenly, and placed on a magnetic stirrer for a magnetic stirring. The reaction is carried out under a UV irradiation, and the reaction progress is monitored by infrared. When the double bond disappears, the reaction ends. The methylene chloride is removed by a rotary evaporator to obtain a light-yellow viscous liquid, namely a tannic acid curing agent (TUC 4).

3.60 g of epoxy resin NPEL 128 is mixed with 3.58 g of the TUC 4, and 1 wt % of tetramethylammonium fluoride is added as a catalyst, mixed evenly to prepare a tinplate coating plate with an actual film thickness of 120 μm to test the impact-resistance strength, bending, hardness and adhesion of the film. An epoxy film with a film thickness of 0.5 mm is prepared in the mould to test the stress-strain and modulus of the film. The tinplate and mould are cured in an oven at 55° C. for 3 h, then 80° C. for 5 h, and then 110° C. for 5 h to obtain an epoxy film, recorded as TEP 4.

Comparative Example 1

3.70 g of epoxy resin NPEL 128 is mixed with 0.68 g of tannic acid (TA), and 1 wt % of tetrabutylammonium bromide is added as a catalyst, mixed evenly to prepare a tinplate coating plate with an actual film thickness of 120 μm to test the impact-resistance strength, bending, hardness and adhesion of the film. An epoxy film with a film thickness of 0.5 mm is prepared in the mould to test the stress-strain and modulus of the film. The tinplate and mould are cured in an oven at 50° C. for 3 h, then 80° C. for 4 h, and then 120° C. for 6 h to obtain an epoxy film, recorded as TEP 0.

The test results of renewable carbon contents and viscosities of various curing agents are shown in Table 1.

Figure 6:
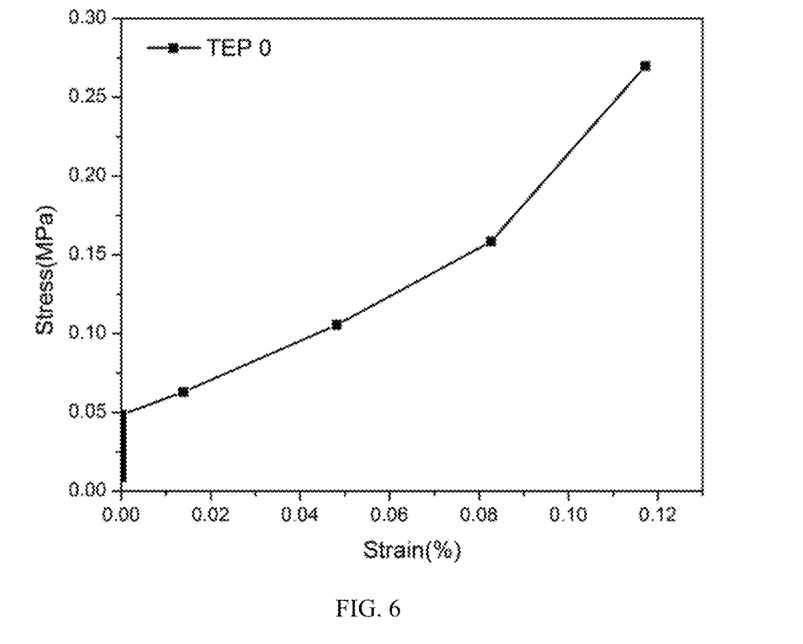
FIG. 6 is a diagram showing a stress-strain curve of TEP 0.
Figure 7:
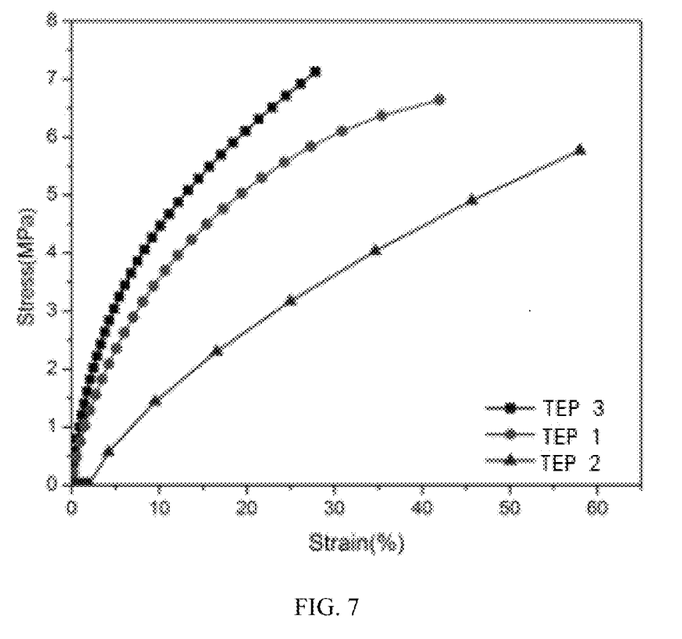
FIG. 7 is a diagram showing stress-strain curves of TEP 1, TEP 2 and TEP 3.
Figure 8:
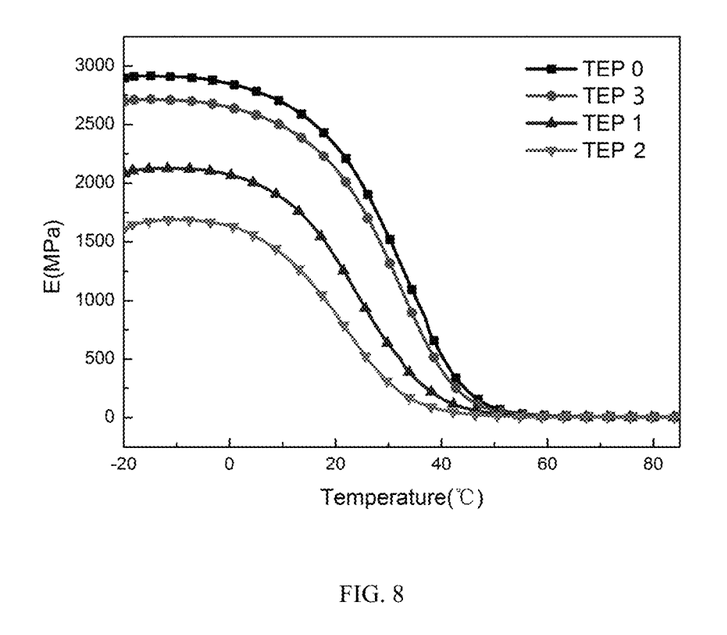
FIG. 8 is a diagram showing modulus curves of tannic acid toughened epoxy films.

The testing properties of the films include pencil hardness, bending, impact (positive/negative), adhesion, gel rate and stress-strain. The test methods refer to the international standards GB/T 6739-2006 *Determination of Film Hardness by Pencil Test*, GB/T 6742-86 *Bend Test for Coating (Cylindrical Mandrel)*, GB/T1732-93 *Determination of Impact Resistance of Film*, GB/T9286-88 *Paints and Varnishes-Cross Cut Test for Films*. The stress-strain and modulus are tested by a dynamic mechanical analyzer (DMA-Q800, TA company, USA). The test results are shown in Table 2 and FIG. 6.

TABLE 1

Renewable carbon content and viscosity of curing agent

| Sample | Renewable carbon content/% | Viscosity/mpa · s |
|---|---|---|
| TA | 100 | — |
| TUC 1 | 86.6 | 410 |
| TUC 2 | 84.0 | 390 |
| TUC 3 | 90.9 | 480 |
| TUC 4 | 89.7 | 460 |

Note:
the temperature for the viscosity test is 70° C.

TABLE 2

Film properties

| Sample | Gel rate/% | Pencil hardness | Adhesion | Bending | Impact (positive/negative) 1 kg · X cm |
|---|---|---|---|---|---|
| TEP 0 | 63.57 | 4 H | — | — | — |
| TEP 1 | 92.38 | 2 H | Grade 0 | 1 mm | 50/50 |
| TEP 2 | 93.04 | 3 H | Grade 0 | 1 mm | 50/50 |
| TEP 3 | 90.12 | 2 H | Grade 0 | 1 mm | 50/50 |
| TEP 4 | 92.67 | 2 H | Grade 0 | 1 mm | 50/50 |

According to the above experimental results, the tannic acid curing agent prepared by this application has been improved in viscosity and gel rate. The minimum pencil hardness is 2 H, and the bending property reaches 1 mm. The tannic acid curing agent prepared by this application has excellent toughness.

The above is only the preferred examples of the present invention. It should be pointed out that, for ordinary technicians in the technical field, a variety of improvements and modifications can be made without departing from the principle of the present invention, and these improvements and modifications shall fall within the protection scope of the present invention.

What is claimed is:

1. A preparation method of a tannic acid curing agent, comprising the following steps:
   (1) mixing tannic acid, 10-undecenoyl chloride, a catalyst and a first solvent for a substitution reaction to obtain undecylenyl tannic acid;
   wherein the catalyst comprises an acid binding agent and 4-diaminopyridine; and
   the first solvent comprises ethyl acetate and N,N-dimethylformamide;
   (2) mixing the undecylenyl tannic acid, a mercapto compound, a second solvent and a photoinitiator for an addition reaction under an ultraviolet irradiation to obtain the tannic acid curing agent;
   wherein the mercapto compound is a mercapto carboxylic acid compound or a mercapto alcohol compound.

2. The preparation method according to claim 1, wherein a molar ratio of the tannic acid and the 10-undecenoyl chloride in step (1) is 1:30-50, and a mass ratio of the tannic acid and the N,N-dimethylformamide is 1:7-10.

3. The preparation method according to claim 2, wherein a mass ratio of the N,N-dimethylformamide and the ethyl acetate in step (1) is 1:1.5-2.5; a mass ratio of the acid binding agent and the ethyl acetate is 1:6-8; and a mass ratio of the 4-diaminopyridine and the acid binding agent is 1:19-22.

4. The preparation method according to claim 3, wherein a reaction temperature of the substitution reaction in step (1) is 30-40° C., a reaction time of the substitution reaction is 20-30 h, and the substitution reaction is carried out in a protective atmosphere.

5. The preparation method according to claim 2, wherein a reaction temperature of the substitution reaction in step (1) is 30-40° C., a reaction time of the substitution reaction is 20-30 h, and the substitution reaction is carried out in a protective atmosphere.

6. The preparation method according to claim 1, wherein a reaction temperature of the substitution reaction in step (1) is 30-40° C., a reaction time of the substitution reaction is 20-30 h, and the substitution reaction is carried out in a protective atmosphere.

7. The preparation method according to claim 1, wherein the mercapto carboxylic acid compound is at least one selected from the group consisting of mercaptoacetic acid, 3-mercaptopropionic acid, thiolactic acid, 2-mercapto-2-methylpropionic acid, 4-mercaptobutyric acid, 3-mercaptoisobutyric acid, cysteine, DL-cysteine, D-cysteine, 3-amino-2-thiopropionic acid, 6-mercaptoacetic acid and 4-mercapto-4-methylvaleric acid.

8. The preparation method according to claim 7, wherein a molar ratio of the undecylenyl tannic acid and the mercapto compound in step (2) is 1:12-21, the photoinitiator is a UV series initiator, an addition amount of the photoinitiator is 0.5-2 wt % of a total mass of the mercapto compound and the undecylenyl tannic acid, the second solvent comprises methylene chloride, the ethyl acetate and ethanol, and a mass ratio of the undecylenyl tannic acid and the second solvent is 1:1-5.

9. The preparation method according to claim 1, wherein the mercapto alcohol compound is at least one selected from the group consisting of 2-mercaptoethanol, 3-mercapto-1-propanol, 1-mercapto-2-propanol, 2-mercapto-1-propanol, 2-mercapto-3-butanol, 4-mercapto-1-butanol, 3-mercapto-2-butanol, 1-thioglycerol, (S)-1-thioglycerol and 3-mercapto-3-methyl-1-butanol.

10. The preparation method according to claim 9, wherein a molar ratio of the undecylenyl tannic acid and the mercapto compound in step (2) is 1:12-21, the photoinitiator is a UV series initiator, an addition amount of the photoinitiator is 0.5-2 wt % of a total mass of the mercapto compound and the undecylenyl tannic acid, the second solvent comprises methylene chloride, the ethyl acetate and ethanol, and a mass ratio of the undecylenyl tannic acid and the second solvent is 1:1-5.

11. The preparation method according to claim 1, wherein a molar ratio of the undecylenyl tannic acid and the mercapto compound in step (2) is 1:12-21, the photoinitiator is a UV series initiator, an addition amount of the photoinitiator is 0.5-2 wt % of a total mass of the mercapto compound and the undecylenyl tannic acid, the second solvent comprises methylene chloride, the ethyl acetate and ethanol, and a mass ratio of the undecylenyl tannic acid and the second solvent is 1:1-5.

12. The preparation method according to claim 11, wherein an irradiance of the ultraviolet irradiation is 5,000-7,000 μW/cm$^2$, a wavelength of the ultraviolet irradiation is 350-395 nm, an irradiation time of the ultraviolet irradiation is 10-14 h.

* * * * *